US011096621B2

(12) United States Patent
Ramadan et al.

(10) Patent No.: US 11,096,621 B2
(45) Date of Patent: Aug. 24, 2021

(54) DETECTION OF BRCA AND OTHER HIGH RISK CARRIERS IN BREAST TISSUE

(71) Applicant: Newcastle Innovation Limited, Callaghan (AU)

(72) Inventors: Saadallah Ramadan, Bexley (AU); Gorane Santamaria, Barcelona (ES); Peter Malycha, St Georges (AU); Carolyn Mountford, East Ryde (AU); David Clarke, Callaghan (AU)

(73) Assignee: TRANSLATIONAL RESEARCH INSTITUTE PTY LTD AS TRUSTEE OF TRANSLATIONAL RESEARCH INSTITUTE TRUST, Woolloongabba (AU)

( * ) Notice: Subject to any disclaimer, the term of this patent is extended or adjusted under 35 U.S.C. 154(b) by 882 days.

(21) Appl. No.: 14/775,909

(22) PCT Filed: Mar. 17, 2014

(86) PCT No.: PCT/IB2014/001593
§ 371 (c)(1),
(2) Date: Sep. 14, 2015

(87) PCT Pub. No.: WO2014/199228
PCT Pub. Date: Dec. 18, 2014

(65) Prior Publication Data
US 2016/0022197 A1 Jan. 28, 2016

Related U.S. Application Data

(60) Provisional application No. 61/800,953, filed on Mar. 15, 2013.

(51) Int. Cl.
*A61B 5/00* (2006.01)
*A61B 5/055* (2006.01)
*G01N 33/483* (2006.01)
*G01R 33/46* (2006.01)
*C12Q 1/6886* (2018.01)
*G01R 33/485* (2006.01)
*G01R 33/465* (2006.01)
*G01R 33/483* (2006.01)

(52) U.S. Cl.
CPC ............ *A61B 5/4312* (2013.01); *A61B 5/055* (2013.01); *A61B 5/7282* (2013.01); *A61B 5/742* (2013.01); *C12Q 1/6886* (2013.01); *G01N 33/4833* (2013.01); *G01R 33/46* (2013.01); *G01R 33/465* (2013.01); *G01R 33/483* (2013.01); *G01R 33/485* (2013.01); *A61B 2576/02* (2013.01); *C12Q 2563/143* (2013.01); *C12Q 2565/601* (2013.01); *G01N 2405/00* (2013.01); *G01R 33/4633* (2013.01)

(58) Field of Classification Search
CPC ..... A61B 2576/02; A61B 5/055; A61B 5/742; A61B 5/7282; A61B 5/4312; G01N 33/4833; G01N 2800/365; G01N 2800/7023
See application file for complete search history.

(56) References Cited

U.S. PATENT DOCUMENTS

| 6,835,572 B1 | 12/2004 | Mountford et al. |
| 8,133,737 B2 | 3/2012 | Krepinsky et al. |
| 2005/0170441 A1 | 8/2005 | Odunsi et al. |

FOREIGN PATENT DOCUMENTS

WO WO-2013049112 A1 * 4/2013 ............ G01N 24/08

OTHER PUBLICATIONS

Ramadan, et al., "Use of in Vivo Two-dimensional MR Spectroscopy to Compare the Biochemistry of the Human Brain to That of Glioblastoma," Radiology, May 2011, 259(2):540-549.
Mountford, et al., "MR spectroscopy in the breast clinic is improving," Eur.J.Radiology, Sep. 2012, 81 Suppl 1:S104-6.
Lean, et al., "Determination of Grade and Receptor Status from the Primary Breast Lesion by Magnetic Resonance Spectroscopy," Technology in Cancer Research & Treatment, Dec. 2004, 3(6):551-556.
Cocuzzo, et al., "Algorithms for Characterizing Brain Metabolites in Two-Dimensional In Vivo MR Correlation Spectroscopy," IEEE, Aug. 2011, 4929-4934.
Stanwell, et al., "Neuro magnetic resonance spectroscopy using wavelet decomposition and statistical testing identifies biochemical changes in people with spinal cord injury and pain," NeuroImage, Jun. 2010, 544-552.
Mackinnon, et al., "Evaluation of an in vitro Invasion Assay for Use on Solid Tissue Samples and Cultured Cells," Invasion Metastasis, Jul. 1992, 12:241-252.
Thompson, et al., "Cancer Incidence in BRCA1 Mutation Carriers," Journal of the National Cancer Institute, Sep. 2002, 94(18):1358-1365.
TBCL Consortium, "Cancer Risks in BRCA2 Mutation Carriers," Journal of the National Cancer Institute, Aug. 1999, 91(15): 1310-1316.
National Cancer Institute, "Genetics of Breast and Ovarian Cancer (PDQ®)," Cancer Information Summary, Dec. 2013, 154 pp.
Fergus, et al., "Breast and Ovarian Cancer in the Ashkenazi Jewish Population," Genetic Health, Aug. 2000, 5 pp.
Kadouri, et al., "Cancer risks in carriers of the BRCA1/2 Ashkenazi founder mutations," J. Med. Genet., Feb. 2007, 44:467-471.
Liotta, et al., "The microenvironment of the tumour-host interface," Nature Medicine, May 2001, 411:375-379.

(Continued)

*Primary Examiner* — Christopher Adam Hixson
(74) *Attorney, Agent, or Firm* — Lucas & Mercanti, LLP (57) ABSTRACT

A method and system for detecting the presence of BRCS carriers in breast tissue, comprises obtaining spectral data from breast tissue using a magnetic resonance spectroscopy device and producing spectral data by said device which provides chemical markers to enable detection of whether the breast tissue contains BRCA carriers.

12 Claims, 3 Drawing Sheets

(56) References Cited

OTHER PUBLICATIONS

Zhang, et al., "Dysregulated lipid metabolism in cancer," World Journal of Biological Chemistry, Aug. 2012, 3(8):167-174.
Scheim, "Cytotoxicity of unsaturated fatty acids in fresh human tumor explants: concentration thresholds and implications for clinical efficacy," Lipids in Health and Disease, Dec. 2009, 8:54 (11 pp.).
Altenburg, et al., "Omega-3 Polyunsaturated Fatty Acids Down-Modulate CXCR4 Expression and Function in MDA-MB-231 Breast Cancer Cells," Mol. Cancer Res., Jun. 2009, 7(7): 1013-1020.
Mackinnon, et al., "Correlation of cellular differentiation in human colorectal carcinoma and adenoma cell lines with metabolite profiles determined by 1H magnetic resonance spectroscopy," Int. J. Cancer, Oct. 1994, 59(2):248-261.
Mackinnon, et al., "Esterified cholesterol and triglyceride are present in plasma membranes of Chinese hamster ovary cells," Eur. J. Biochem., Apr. 1992, 205(2):827-839.
Wright, et al., "Phospholipid and Ether Linked Phospholipid Content Alter with Cellular Resistance to Vinblastine," Biochem. Biophys. Res. Comm., Dec. 1985, 133(2):539-545.
Bathen, et al., "MR-determined metabolic phenotype of breast cancer in prediction of lymphatic spread, grade, and hormone status," Breast Cancer Res Treat, Oct. 2006 epub, 104:181-189.
Ramadan, et al., "Two-Dimensional Magnetic Resonance Spectroscopy on Biopsy and In Vivo," Annual Reports on NMR Spectroscopy, Dec. 2009, 65:161-199.
Stanwell, et al., "In Vivo Proton MR Spectroscopy of the Breast," Radio Graphics, Oct. 2007, 27:S253-S266.
Stanwell, et al., "Specificity of choline metabolites for in vivo diagnosis of breast cancer using 1H MRS at 1.5 T," Eur. Radiol., Sep. 2004 epub, 15:1037-1043.
Ramadan, et al., "In vivo 1D and 2D correlation MR spectroscopy of the soleus muscle at 7T," J. Magnetic Resonance, Feb. 2010, 204:91-98.
Velan, et al., "Detection of Cerebral Metabolites by Single-Voxel-Based PRESS and COSY Techniques at 3T," J. Magnetic Resonance, Aug. 2007, 26(2):405-409.
Lipnick, et al., "Combined DCE-MRI and single-voxel 2D MRS for differentiation between benign and malignant breast lesions," NMR in Biomedicine, Apr. 2010 epub, 23:922-930.
Somorjai, "Creating robust, reliable, clinically relevant classifiers from spectroscopic data," Biophys. Rev., Nov. 2009, 1(4):201-211.
Schnall, et al., "Diagnostic Architectural and Dynamic Features at Breast MR Imaging: Multicenter Study," Radiology, Jan. 2006, 238(1):42-53.
Ogg, et al., "WET, a $T_1$ - and $B_1$ -insensitive water-suppression method for in vivo localized $^1$H NMR spectroscopy," J. Magn. Reson. Series B, May 1994, 104(1):1-10.
Govindaraju, et al., "Proton NMR chemical shifts and coupling constants for brain metabolites," May 2000, 13(3):129-153.
Lean, et al., "Cell-Surface Fucosylation and Magnetic Resonance Spectroscopy Characterization of Human Malignant Colorectal Cells," Biochemistry, Nov. 1992, 31(45):11095-11105.
Liu, et al., "Statistical Analysis of Two Dimensional MR Spectroscopy Combined with Dynamic Contrast Enhanced MRI in Breast Cancer Detection," Proceedings of the International Society for Magnetic Resonance in Medicine, 17th Annual Meeting and Exhibition, Apr. 18, 2009, p. 4237.
Liu, et al., "Breast Tissue Classifications by CART Analysis of Localized 2D COSY," Proceedings of the International Society for Magnetic Resonance in Medicine, 17th Annual Meeting and Exhibition, Apr. 18, 2009, p. 4327.
Liu, et al., "Turbo-Spin-Echo Based Correlated Spectroscopic Imaging of Breast Tissues in Vivo: A Preliminary Study," Proceedings of the International Society for Magnetic Resonance in Medicine, 17th Annual Meeting and Exhibition, Apr. 18, 2009, p. 4284.
Thomas, et al., "Two-Dimensional MR Spectroscopic Characterization of Breast Cancer In Vivo," Technology in Cancer Research and Treatment, Feb. 2005, vol. 4, No. 1, pp. 99-106.
Ramadan, et al., "Distinction of Invasive Lobular Carcinoma, Invasive Ductal Carcinoma, and Healthy Breast Tissue In Vivo With L-COSY at 3T," Proceedings of the International Society for Magnetic Resonance in Medicine, May 7, 2011, p. 1037.
Ramadan, et al., "Lipid and Metabolite Deregulation in the Breast Tissue of Women Carrying BRCA1 and BRCA2 Genetic Mutations," Radiology, Jun. 1, 2015, vol. 275, No. 3, pp. 675-682.
Nov. 4, 2016 supplementary European search seport in European Patent Application No. EP14810941.6, European phase of PCT/IB2014/001593, of which this application is the US national stage.
Nov. 14, 2016 Communication of the extended European search report in European Patent Application No. EP14810941.6.
Dec. 1, 2016 Communication to reply to supplementary European search report in European Patent Application No. EP14810941.6.
Jun. 1, 2017 response to Dec. 1, 2016 Communication European Patent Application No. EP14810941.6, including claim amendments.
Thomas, A.M. et al., Volume-Localized Two-Dimensional Correlated Magnetic Resonance Spectroscopy of Human Breast Cancer, Journal of Magnetic Resonance Imaging, Mar. 2001, 14: 181-186.
Thomas, A.M. et al., Investigation of Breast Cancer Using Two-Dimensional MRS, NMR in Biomedicine, Dec. 2008 (online), 22: 77-91.
Ramadan, S. et al., L-COSY of Breast Cancer at 3T, European Journal of Radiology, Sep. 2012, 81(1): S129-S131.
International Search Report dated Feb. 24, 2015 in PCT/IB2014/001593 (international phase of present application).
Written Opinion dated Feb. 24, 2015 in PCT/IB2014/001593 (international phase of present application).

* cited by examiner

DETECTION OF BRCA AND OTHER HIGH RISK CARRIERS IN BREAST TISSUE

CROSS-REFERENCE TO RELATED APPLICATIONS

This application claims priority on U.S. provisional application Ser. No. 61/800,953 filed Mar. 15, 2013, which is incorporated by reference herein.

BACKGROUND OF THE INVENTION

The present application relates to detection of altered breast tissue chemistry.

Within this patent application, citations are made to prior publications. These are incorporated by reference herein.

BRCA1 and BRCA2 are human suppressor genes that appear in normal cells. In normal cells BRCA1 and BRCA2 help ensure the stability of the cell's DNA and help prevent uncontrolled cell growth.

Mutations in these BRCA1 and BRCA2 genes disrupt the protection mechanism and also cause an increase in hereditary breast and ovarian cancer (8,9). If a woman inherits a deleterious mutation in either BRCA1 or BRCA2 mutation gene her risk of breast and ovarian cancer increases. Men who inherit these mutation genes also have an increased risk of breast cancer.

Approximately 12% of women will develop breast cancer sometime during their lives compared with about 60% of women with a harmful mutation in a BRCA mutation. Thus, a woman with a BRCA1 or BRCA2 gene mutation is about 5 times more likely to develop breast cancer than a woman who does not have such a gene mutation.

Compared to breast cancer, ovarian cancer is relatively rare but has a poorer prognosis. It occurs in 1-2% of the general population compared with 15 to 40% with a BRCA1 or BRCA2 gene mutation (9, 10).

At least one segment of the population, Ashkenazi Jewish women, have a 1/40 risk of carrying a BRCA1 or BRCA2 gene mutation compared with 1/450 risk in the general population (10-12).

SUMMARY OF THE INVENTION

The invention provides a method using in vivo and ex vivo 2D Magnetic Resonance Spectroscopy (MRS) to distinguish breast tissue chemistry from BRCA1 and BRC2 carriers from healthy controls and from invasive cancer. Altered biochemical state(s) have been proposed to exist in the breast tissue of women with BRCA gene mutations constituting preinvasive conditions. A method to objectively diagnose such conditions has, until now, remained elusive.

It has been determined that breast tissue having BRCA1 and BRCA2 gene mutations have different chemistry compared to the chemistry of healthy control tissue and invasive cancers. The difference can be seen using a non-invasive virtual biopsy, i.e., using a two dimensional magnetic resonance spectroscopy (2D MRS) on a clinical MR scanner.

Despite no evidence of any changes to breast tissue from current imaging modalities, the 2D MRS method identifies three preinvasive stages to exist in women carrying the BRCA gene mutations. These include an increase in the amount and level of unsaturation of fatty acids and triglyceride and the appearance of cholesterol in the tissue. The other is a reduction MR visible metabolic substrates. These precede the well established activation of choline metabolism through the choline kinase and phospholipase C over expression. Importantly BRCA1 differs from BRCA2 in the order of events. These findings, recorded in vivo, are supported by results from a well characterized cell model of tumorigenesis and indicate that when all three changes are present the tissue is one final step away from malignancy (16).

Biopsies can be taken from volunteers and patients and a high resolution 2D MR spectrum undertaken to look for any other low levels of metabolites that may be present but not apparent in vivo. The biopsies correlate with modern molecular genetics analysis. The new findings were consistent with reports that a lipid environment or optimal malignant tumor growth exists. Until now there was no means to document such an environment in vivo.

The BRCA1 and BRCA2 gene mutations can also be detected in ex vivo tissue using a core or fine needle biopsy of tissue, where the fat is included in the tissue. The tissue could be analyzed using a two dimensional magnetic resonance spectroscopy (2D MRS) in a narrow bore NMR spectrometer.

The obtained data strongly indicate that the BRCA carriers have breast tissue with increased unsaturated lipid and increased membrane cholesterol which is conducive to tumor growth. This effectively constitutes premalignant conditions in BRCA carriers not previously reported. The MR methods can be used to look for very early changes in metabolites indicative of early malignancy.

BRIEF DESCRIPTION OF THE DRAWINGS

STRUCTURE 1

FIG. 1 shows a 2D MR spectrum from:

A) Healthy control on the left hand side with the crosspeaks assigned "A-F" as shown in STRUCTURE 1.

B) Typical apparently healthy BRCA1 mutation carrier on the right hand side. The assignment "Z" for the methyl & methine alkyl side chain cholesterol ring is marked.

DETAILED DESCRIPTION OF A PREFERRED EMBODIMENT

A preferred embodiment of the invention will be described as one means of practicing the invention.

However, the present invention is not limited to this embodiment.

The present invention involved the collection and analysis of spectral data to distinguish breast tissue of women with BRCA1 and BRCA2 from the control cohorts of healthy and those with invasive cancers based on altered chemistry including lipid composition. The same approach can be used in two dimensional (2D) magnetic resonance (MR) COrrelated SpectroscopY (COSY) MRS technique (1, 2) method to distinguish breast tissue of women with BRCA1 and/or BRCA2 from the control cohorts of healthy and those with invasive cancers based on altered lipid composition and presence or absence of other metabolites. The 2D MRS protocol may be collected on a 3 Tesla clinical MR scanner, or scanner at higher magnetic frequency, results can produce informatics bio algorithms that will enable the technology to be widely available. Biopsies taken from each category can be analyzed by Molecular Genetics and high resolution MR spectroscopy to look for the changes recorded in vivo and for other metabolites present in lower concentrations.

The study according to the present invention established that:
1: Women carrying the BRCA1 and or the BRCA2 gene mutations can exhibit changes to lipid chemistry that include increased levels of unsaturation; increased triglyceride, appearance of cholesterol in the spectrum and a reduction in the substrates. This is different to healthy tissue and to benign tissue and to and to invasive carcinoma. These changes precede the choline kinase and phospholipase C over expression; cannot be identified using current imaging modalities; and these do not necessarily appear in the same order in each person.
2: An algorithm for each of these stages can allow the diagnosis to be made available on a commercial 3T MR scanner or magnet of higher frequency such as 4 or 7T.
3: The BRCA1 and BRCA2 groups have an MR detectible pre-invasive conditions, based on altered lipid composition and substrates that are not recognized by conventional light microscopy but may be identified by modern molecular genetics.
4: The lipid composition of the BRCA1 and BRCA2 breast tissue has increased unsaturated lipid and increased triglyceride making it more susceptible to a cancerous growth.
5. The BRCA1 and BRCA2 groups show a reduction in glycerol, inositol and glycine (substrates). These occur prior to the choline kinase and phospholipase C over expression.

One can practice the invention by recording single voxel 1D and 2D MRS data in a cohort of:
BRCA1 and/or BRCA2
Healthy age matched controls with no family history of breast cancer
Benign lesions
Invasive cancers One can develop bio informatics algorithms like or similar to those disclosed in U.S. Pat. No. 6,835,572, incorporated by reference herein.

Using 2D chemical shift imaging one can identify changes across the breast of BRCA patients which include the appearance of metabolites indicative of a benign or DCIS with or without micro invasive disease. If located a 2D COSY can be undertaken. An MR image guided biopsy can be taken for conventional histology, molecular genetics and in vitro MRS to determine the levels of metabolites present or chemistry indicative of nodal involvement.

The inventors herein have been integral to the development and clinical application of in vivo 2D COrrelated SpectroscopY (COSY) MRS technique (1), which is now in operation in a breast clinic. The inventors herein have developed a breast biopsy method that can predict nodal involvement purely on the chemistry of the primary tumor (3), and have developed an "algorithm suite" (see U.S. Pat. No. 6,835,572). Siemens Healthcare has collaborated to develop the operational software to study small lesions (LT 5 mm) in the breast (6). The inventors have also undertaken chemical analyses of cells and biopsies to understand the role of lipids in tumor development and progression (7).

According to the invention, one can detect chemical indicators within the breast cells of a BRCA1 or BRCA2 carrier that are different from each other in the order of appearance and from a non carrier. A BRCA1 and BRCA2 carrier is really a condition in which a "field change" exists making whole breast vulnerable to cancer. In order to fully understand the type of chemistry that is altering the tissue by a comparison with healthy controls with no family history of breast cancer, one can compare the chemistry of a BRCA1 and BRCA2 carriers with the pathologically well documented benign, and infiltrating ductal and lobular cancers.

It has been suggested that a lipid environment exists for malignant tumor growth and inhibition (13). Alteration of lipid metabolism has been increasingly recognized as a hallmark of cancer cells (14) and importantly well documented cell models of colorectal tumor development (17). The changes of expression and activity of lipid metabolizing enzymes are directly regulated by the activity of oncogenic signals. Lipid targeting in cancer therapy is growing in interest because of a reawakened appreciation for the role of metabolic pathways as essential features of malignant transformation and progression (14). The present invention provides a method of evaluating the lipid in the breasts of at-risk women.

In inventors earlier work, lipids were found to play an important role in tumor development and progression and these were documented both by MRS on cells and biopsies and by the chemical analysis of whole cells and purified plasma membranes (17-19). There the chemistry of the plasma membranes of a series of ovarian cell lines (18) showed that the MR spectra reflected differences in the chemical composition of the plasma membrane rather than the whole cell. The chemical differences were found to be associated with a reduction in membrane mobility, and thus a reduction in the intensity of the lipid in the MR spectrum occurred with free cholesterol levels increasing by over ⅓. Although the amount of esterified cholesterol remained comparable, the fatty-acyl-chain composition contained significantly higher proportions of most of the saturated fatty acids, particularly 16:0. Thus increased levels of saturated cholesterol esters altered the membrane structure and thus the MR spectrum. This observation is important when considering the results described below from our study of women who carry the BRCA genes.

The chemistry of a primary breast tumor is indicative of both the pathology and the spread of the disease to the lymph nodes. The information available included: pathology, nodal involvement, receptor status and vascularization (3, 20). Details can be found in U.S. Pat. No. 6,835,572.

A 2D MRS was undertaken on cultured cells and diseased tissues that were being biopsied for clinical reasons. Here, the correlation with cell biology and histopathology was relatively straightforward, despite the need for serial-sectioned histopathology (21). From these 2D MRS studies the chemicals, including detailed chemical analysis of lipids, involved in specific aspects of tumor development and progression, were documented.

The use of two-dimensional (2D) Localized (L) Correlated SpectroscopY (L-COSY) for the breast examination overcame issue of fat and it also allowed the fat itself to become a diagnostic factor (6). L-COSY utilizes a simple three-pulse sequence:
90ϕ1-90ϕ2-t1-90ϕ3-Acq (ϕ is phase)
(or permutation thereof) whereby each spectrum is acquired in succession and t1 is incremented by a set value. This change in echo time provides a second time domain which can then be Fourier transformed to provide a two dimensional spectrum. In a 2D L-COSY spectrum, a crosspeak off the diagonal indicates scalar coupling between the two protons it connects on the diagonal, thus providing chemical specificity not available to conventional 1D MRS. Using data collected in a whole body commercially available scanner at 3T, there is more molecular information now open for inspection in the breast using the L-COSY method which has been applied successfully to other organs including brain, glioma (1) and muscle (24). The advantage of L-COSY is that it allows for unambiguous identification of metabolites and lipids with lower Cramér-Rao lower bounds variance, compared to the 1D spectra (25).

Figure 1:
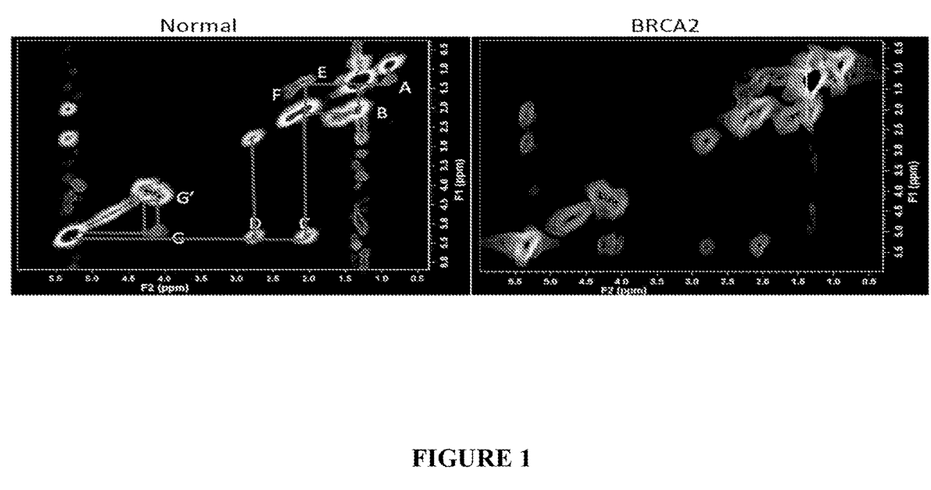

FIG. 1 shows a 2D COSY of a healthy breast and that from a BRCA gene carrier. In a COSY spectrum a cross peak, off the diagonal, indicates scalar coupling between the two protons it connects on the diagonal. In FIG. 1 the cross peaks A-G and G' can be traced as assigned as seen in the structure of triglyceride at the top of FIG. 1. Crosspeaks D and C are the olefinic linkages next to the double bonds. Thus the ratio of these unsaturated moieties present can be measured and compared with the total —C=C— at 5.2 ppm on the diagonal. The L-COSY from the healthy breast has no resonances on the diagonal between 3 and 4 ppm consistent with the absence of tumor (26, 27). Crosspeak "Z" is from the methyl and methine protons of the alkyl side chain of the cholesterol ring system. The appearance of this crosspeak indicates the absence of cholesterol and/or cholesterol ester in an MR visible neutral domain.

Figure 2:
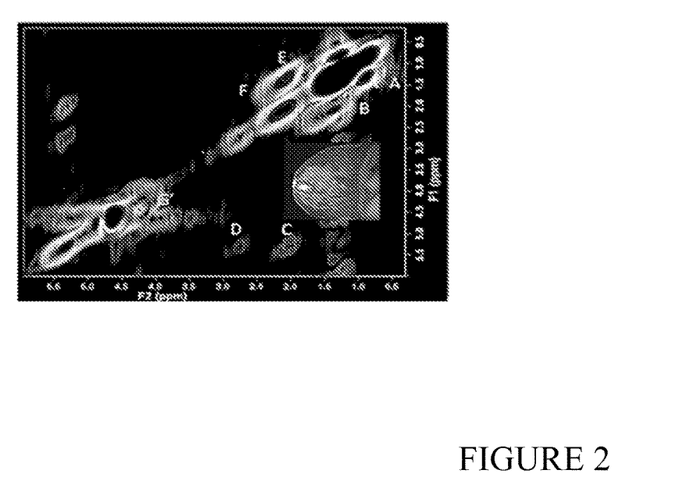
FIG. 2 shows a COSY from a malignant lesion (left), using same parameters as in FIG. 1, and a COSY from a choline region shown expanded (right), showing three resonances on the diagonal at 3.0-3.4, 3.23, 3.28 and 3.40 ppm.

FIG. 2 shows the L-COSY from a malignant tumor. The same triglyceride crosspeaks A-G are seen but olefinic crosspeaks D and C are complex and made up of several components. In this L-COSY, on the diagonal, the resonance at 3.23 ppm from the choline can be seen. In FIG. 2 the choline region is expanded and resonances at 3.23, 3.28 and 3.40 ppm are apparent on the diagonal.

Three healthy subjects (Ave=31 yrs, SD=11 yrs), one BRCA1 (Ave=53 yrs) and two BRCA2 (Ave=51 yrs, SD=2 yrs) were scanned on a 3 tesla Skyra (Siemens, Erlangen) whole body magnet. Although a Siemens Skyra scanner was used, other scanners can be used. All subjects were positioned prone (head first) with their breasts inside a 16-channel receive-only coil while body coil was used for RF transmission. A 1×1×1 cm$^3$ voxel was positioned in the fatty part of the breast and a 2D spectroscopic (L-COSY) data was acquired and processed identically as described elsewhere (28). A typical processed, L-COSY BRCA spectrum acquired is shown in FIG. 1 on the right side. The crosspeaks and diagonal resonances recoded from the BRCA1 and BRCA2 showed strong discriminators between healthy and BRCA groups. No difference was seen between BRCA1 and BRCA2.

Figure 3:
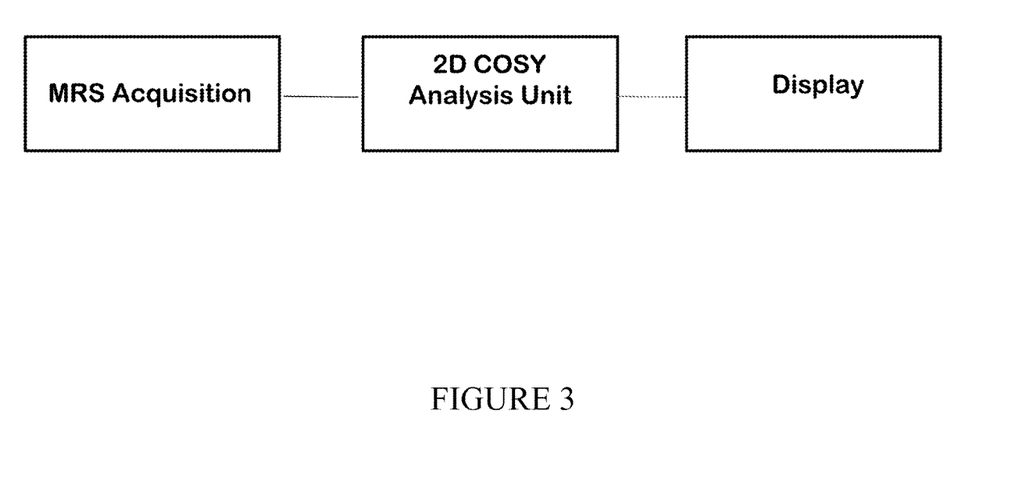
FIG. 3 shows a block diagram of a system that may be used to practice the invention.

FIG. 3 shows a summary of the results. From the small number of subjects, peaks 8 (4.7-4.7 ppm), 9 (5.4-5.4 ppm), 13 (1.3-1.3 ppm), 14 (2.1-1.3 ppm) and 17 (2.3-1.6 ppm) were identified to be distinguish between the control and BRCA1/BRCA2 groups. The molecular lipid moieties represented by these peaks is shown in FIG. 3.

FIG. 1 shows COSY from healthy breast tissue (left) and breast tissue of BRCA2 carrier (right). Structure of triglyceride molecule is shown and the cross peak connectivities are indicated for comparison with the L-COSY. There are strong visual and measurable difference between the BRCA1, BRCA2 and the healthy cohort see Table 1 and (FIG. 1).

TABLE 1

Summary of Differences between the BRCA categories and Healthy Controls
(Ratios are to the crosspeak at F2 = 5.3 and F1 = 5.3 ppm)

| | | Percent Difference Compared To Healthy Controls (p-Value) | | | (S/N** ratio GT 50) |
|---|---|---|---|---|---|
| Molecule (N) | —CH—CH2 Triglyceride backbone | CH=CH—CH2—CH=CH— Fatty acyl chain double bonds | | Gycine, Inositol & Glycerol | methyl & methine alkyl side chain cholesterol ring |
| Crosspeak | G (4.12-5.35 ppm) | D (2.70-5.31 ppm) | | Diagonal (3.5-3.5 ppm) | Z (0.9-1.5 ppm) |
| BRCA Combined (N = 23) | +49(0.02)* Altman N = 16 | 24(.010)* Altman N = 13 | | −43(.098) Altman N = 80 | 14/23 |
| BRCA2 (N = 14) | +34(0.08)* Altman N = 21 | +30(.019)* Altman N = 11 | | −27(0.410) Altman N = 250 | 9/14 |
| BRCA1 (N = 9) | +70(.122) Altman N = 11 | +18(.112) Altman N = 29 | | −65(.009)* Altman N = 23 | 5/9 |

*Significance level of P = 0.05 with a power of 95%

**S/N ratio GT 50 was calculated by evaluating the ratio of the cross peak in question to another region of equal size in empty region of the 2D spectrum.

Thus lipids are an important aspect in tumor development and progression. Thomas, et al has suggested that the lipid itself may be diagnostic based on L-COSY methods of the breast (29) and this is consistent with our own results where we analyzed the chemical makeup of whole cells and purified plasma membranes (18). The spectral differences here are consistent with a significant increase in saturated fatty acyl chains on the cholesterol esters and a significant increase in total cholesterol in these membranes. These lipids affect the membrane structure and in turn cause a change in the molecular motion of the membrane lipids which is seen to alter the in vivo spectrum of the breast tissue in BRCA carriers. Importantly by analogy with the ovarian cell study the MR spectra from the BRCA cohort are indicative of an increase in cholesterol and saturated fatty acyle chains on the cholesterol esters (18).

A study was undertaken to detect invasive ductal cancer (IDC) and invasive lobular cancer (ILC). Five patients with benign masses (average age=42 yrs, SD=16 yrs), six patients with IDC (average age=48 yrs, SD=14 yrs), and four healthy female subjects who were recruited as healthy controls (average age=28 years old, SD=5 years). Based on the choline to creatine ratio all cases of IDC and ILC were correctly diagnosed as malignant. To detect the difference between IDC and ILC, the ratio of lipid diagonal and cross-peaks were measured relative to the choline resonance at 3.23 ppm. The ILC had increased levels of MR mobile lipid, compared with IDC. The distinction between ILC and IDC carcinoma was statistically significant, despite very small numbers (28). Thus invasive cancers can constitute a control category for a BRCA study. The lobular cancers that have a much better prognosis appear to have increased levels of unsaturated lipids compared with their ductal counterparts.

In summary, our data indicate that BRCA1 and BRCA2 carriers have breast tissue with a MR spectrum indicative of increased levels of unsaturated lipids, increased triglycerides and in some increased cholesterol consistent with established models of tumor development and making it more susceptible to a cancerous growth. Some also show a reduction in the levels of glycerol, inositol and glycine (substrates). This is in contrast to healthy tissues. This suggests that the BRCA1 and BRCA2 groups have an MR detectible pre-invasive condition that is not recognized by conventional light microscopy but identified by modern molecular genetics on biopsy. These changes appear to occur in a different order in BRCA1 and BRCA2.

An analysis unit analyzes the spectral data.

Further study can be made as described below.

Five cohorts can be studied (BRCA1, BRCA2, benign, healthy controls and invasive cancers), each of which can undergo the following:

1. Recruitment, clinical records and mammography and contrast enhanced MRI;
2. In vivo imaging to include 2D MRS;
3. The BRCA1 and BRCA2 patients can also have 2D chemical shift imaging to identify any changes across the breast which include the appearance of metabolites indicative of a benign or DCIS with or without micro invasive disease;
4. If a lesion is located in the BRCA1 or BRCA2 cohort, 2D COSY can be undertaken. An MR image guided biopsy can be taken for conventional histology, molecular genetics and in vitro MRS to determine if there are low levels of metabolites present or chemistry indicative of nodal involvement (3) (see U.S. Pat. No. 6,835,572);
5. A fine needle aspiration biopsy of apparently healthy tissue can be taken from the control and healthy BRCA groups and from the lesion for the benign group. An intra-operative biopsy can be obtained from invasive cancer group of the primary lesion and normal tissue;
6. Molecular genetics on biopsy can be undertaken;
7. In vitro MRS on biopsy;
8. The imaging can be read and the MRS can also be read;
9. At completion of the data collection the MRI can be reread;
10. De-identified data can be analyzed by an algorithm suite method and can include in vivo and in vitro MRS, genetics, DTI and clinical records;
11. The algorithm method can be tested against new cases to assess its accuracy;
12. The algorithm method can be sent to other sites for testing, including a site where there is a large Ashkenazi Jewish population, and another a site where there is a large breast clinic.

To acquire an adequate breast specimen, fine needle biopsies can be performed with typically six passes with a 23-gauge to provide adequate cells. Tissue from the aspiration site (3 $mm^3$) will be collected for correlative histopathologic analysis for those intraoperative biopsies.

Cells or tissue specimens can be placed in polypropylene vials that contained 300 ply of phosphate-buffered saline in deuterium oxide. All specimens can be immediately immersed in liquid nitrogen and stored at −70 C for up to 6 weeks until MR spectroscopic analysis.

The following are standard exclusion criteria and MR contraindications: electrical implants such as cardiac pacemakers or perfusion pumps; ferromagnetic implants such as aneurysm clips; surgical clips; prostheses; artificial hearts; valves with steel parts; metal fragments, shrapnel, tattoos near the eye, or steel implants; ferromagnetic objects such as jewelry or metal clips in clothing; pregnant volunteers; subjects less than 18 years of age.

At completion, develop mathematical classifiers (30) can be developed to provide a robust pattern recognition tool to allow distinction between BRCA carriers and healthy cohorts. One can look to see if any differences are identified between the BRCA1 and BRCA2 groups.

The MR Data can be collected on a standard clinical 3T scanner (Prisma, Skyra, Verio) or other higher frequencies using a sixteen channel breast coil (Siemens AG, Erlangen, Germany). They can also be undertaken on General Electric and Phillips scanners. One can use an axial, fat suppressed, T2-weighted (T2w) turbo spin echo sequence (repetition time 4000-msec, echo time 96-msec, section thickness 3.0-mm) and an axial 3D T1-weighted gradient-echo sequence (repetition time 6.5-msec, echo time 2.6-msec, section thickness 1.0-mm, Grappa factor of 2) to determine where to place the region of interest.

As used herein, the term "MRS acquisition unit" means a clinical magnetic resonance spectroscopy device which acquires spectral data. As used herein, the term "2D analysis unit" means a spectral analyzer which analyzes the spectral data obtained from tissue of a subject in a 2D format.

Axial images can be acquired at three b-values (50, 400, 800 $s/mm^2$) along read (r), slice (s), phase (p) and trace (t) orientations using a fat suppressed Spectral Adiabatic Inversion Recovery (SPAIR) acquisition with a Fob 148*339 mm (96*220 pixel). Slice thickness 5 mm, number of slice 20, slice separation 6 mm, averages 4, bandwidth 1515 Hz, GRAPPA factor 2, monopolar, TE/TR 72/4000 ms. ADC Trace maps can be automatically calculated on the scanner.

For reading of breast MRI, breast MRI scoring systems are well described in the literature (31). Independent review of all breast MRIs can be taken.

An imaging series can be used to position the voxel for the MRS study. A single voxel (TR/TE: 2000/135 ms, PRESS, 128 averages) can be acquired from the tumor region using a 10×10×10 mm$^3$ voxel. An automatic prescan can be used to adjust frequency, transmitter voltage, water suppression and shimming. Manual first-order shimming can be used to optimize Bo homogeneity at the ROI with the criteria of a minimum magnitude water line width of 20 Hz or less in every subject. This is equivalent to 14 Hz full width half max of water in the real and phased fast Fourier transform of the free induction decay which is nearly equal to 0.01 ppm at 3 Tesla, ensuring adequate line widths for the complete resolution of all metabolites. Scan time can be approximately 4.5 minutes. Raw data can be saved and exported for analysis. Thus, data can be collected with and without water suppression. Data can be sent for classifier development.

2D L-COSY can be acquired with a 16 channel breast coil or with a breast coil with a greater number of channels. Localized shimming can be performed by automatic adjustment of zero- and first-order shim gradients using the automatic B0-field mapping technique (Siemens AG, Erlangen, Germany) followed by manual adjustment of zero-order shim gradients to achieve width of water at half-maximum to less than 14 Hz. Following frequency adjustment water-selective suppression can be optimized using the WET-technique (32). Shimming a volume slightly bigger than ROI can provide a better shim, therefore automatic and manual shimming can be initially conducted with a 30×30×30 mm$^3$ shim volume, and then optimized for the interrogated voxel size. The L-COSY sequence can be applied with a FE (initial) of 30 ms, TR of 1.25 sec, 8 averages per increment, spectral width in F2 will be 2000 Hz, t1 increment size of 0.8 ms, indirect spectral width used can be 1250 Hz and the number of increments can be 64. The "WET" water suppression method (32) can applied before the acquisition sequence. The acquisition time can be 11 min.

Commercial 2D spectral processing software (Felix-2007, Accelrys, and San Diego, Calif., USA) can be used for spectral processing and analysis. The analysis unit could comprise the spectral processing software run on a server-side product that runs on Linux or SGI workstations or as a desktop product for Windows PCs. The processing parameters used can be: F2 domain (skewed sine-squared window, 2048 points, and magnitude), F1 domain (sine-squared window, linear prediction to 90 points, zero-filling to 512 points, magnitude) using Felix software version 2007. The (CH2)n methylene resonance at 1.30 ppm can be used as an internal chemical shift reference in F1 and F2 (33). All cross peaks are denoted with F2F1 in ppm units. The analysis unit compares the spectra obtained to reference spectra for healthy tissue to determine whether the spectra obtained shows a change in the degree and extent of MR recordable lipid saturation or increase in triglyceride levels, an increase in MR visible cholesterol, and/or change in the type and level of metabolic substrate relative to those values for normal tissue. If the values for the spectral data are different from that for normal healthy tissue, a practitioner can fairly conclude that the subject from whom the spectral data was obtained is a carrier of a mutation in the BRCA1 and/or BRCA2 genes that leads to a predisposition to breast cancer.

In vivo breast MRS can be read. All the reads can be done blinded to each other's interpretation, and entered into the database. This can be undertaken in three ways: 1. By visual inspection and resonance ratios to be calculated. 2. Measurement and assignment of the crosspeak volumes of various chemicals as described in Lean et al (34). 3. Data can be sent to the Draper Labs for classifier development.

In vitro MRS: 1D and 2D COSY can be undertaken using 8.5T or higher magnetic frequency magnet NMR spectrometers or above as previously described (3, 35). The data can be analyzed both manually and by the algorithm suite.

According to the invention, the ability to detect BRCA gene carriers (women who have been shown to have a pathogenic mutation in either BRCA 1 or 2), by using a spectral alteration identifiable from a voxel of a breast MRI investigation opens up many opportunities. One may be able to recognize these spectral changes in a larger cohort of patients using normal and malignant breast tissues as controls. The invention also provides a way to detect a diagnostically recognizable spectral difference between ductal and lobular cancer. MRS can be used to identify the signals and hence chemistry that causes up to 60% of BRCA carriers to develop breast cancer. Recent work with 2D MRS can be used to not only identify the molecular variations associated with breast cancer but also name them. The invention can thus be very important in determining the chemical changes that are necessary for a cell to change from being normal to one of three stages of premalignancy or fully malignant. MRS may be able to identify what is already present in BRCA patients and also determine when the risk of cancer increases. Young women who are shown to be BRCA carriers face the dilemma as to when or whether they have prophylactic mastectomy. Usual questions would include whether is it safe to wait until she has had children, breast fed her babies and then undergo surgery. Similarly, as not all women who carry a mutation get breast cancer, one may be able to identify a group at lesser risk. Using the invention can provide valuable insight into the biology of BRCA carriers; a means of identifying which women are at risk biologically and not just as known carriers and when the cancer is developing. The results may also allow an oncology investigator to develop and plan therapeutic measures based on managing the lipid abnormalities that are the pre-invasive state.

Although one embodiment of the invention has been described, the invention is not limited to this embodiment, and modifications to the embodiment may be apparent to those in the art. The scope of the invention is defined only by way of the claims, and not the preferred embodiment.

REFERENCES

1. Ramadan S, Andronesi O, Stanwell P, Lin A, Sorenson G, Mountford C. In Vivo Two Dimensional MR Spectroscopy Compares the Biochemistry of the Human Brain and Glioblastoma. Radiology 2011; 259:540-549.
2. Mountford C E, Schuster C, Baltzer P A T, Malycha P, Kaiser W A. MR spectroscopy in the breast clinic is improving. European Journal of Radiology 2012; 81:S104-S106.
3. Lean C, Doran S, Somorjai R L, et al. Determination of grade and receptor status from the primary breast lesion by magnetic resonance spectroscopy. Technology in Cancer Research & Treatment 2004; 3:551-556.
4. Cocuzzo D, Keshava N, Lin A P, Ramadan S, Mountford C. Algorithms for Characterizing Brain Metabolites in Two-Dimensional in Vivo MR Correlation Spectroscopy. IEEE 2011:4929-4934.
5. Stanwell P, Siddall P, Keshava N, et al. Neuro magnetic resonance spectroscopy using wavelet decomposition and statistical testing identifies biochemical changes in people with spinal cord injury and pain. Neuroimage 2010; 53:544-552.
6. Mountford C, Schuster C, Baltzer P, Malycha P, Kaiser W A. MR Spectroscopy in the Breast Clinic is Improving. European Journal of Radiology 2012; September 2012.
7. Mackinnon W B, Hancock R, Dyne M, Russell P, Mountford C E. Evaluation of an in vitro invasion assay for use on solid tissue samples and cultured cells. Invasion & Metastasis 1992; 12:241-252.
8. Thompson D, Easton D F, Consortium tBCL. Cancer Incidence in BRCA1 Mutation Carriers. Journal of the National Cancer Institute 2002; 94:1358-1365.
9. Consortium TBCL. Cancer Risks in BRCA2 Mutation Carriers. In: Journal of the National Cancer Institute, 1999; 1310-1316.
10. National Cancer Institute; Bethesda M. Genetics of Breast and Ovarian Cancer (PDQ). In: Cancer Information Summary, 2013.
11. Fergus K, Simonsen J. Breast and Ovarian Cancer in the Ashkenazi Jewish population. In, 2013.
12. Kadouri L, Hubert A, Rotenberg Y, et al. Cancer risks in carriers of the BRCA1/2 Ashkenazi founder mutations. Journal of Medical Genetics 2007; 44:467-471.
13. Liotta L A, Kohn E C. The microenvironment of the tumour-host interface. Nature Medicine 2001; 411:375-379.
14. Zhang F, Du G. Dysregulated lipid metabolism in cancer. World J Biol Chem 2012; 3:167-174.
15. Scheim David E, Cytotoxicity of unsaturated fatty acids in fresh human tumor explants: concentration thresholds and implications for clinical efficacy. Lipids in Health and Disease 2009; 8:54.
16. Altenburg J D, Siddiqui R A. Omega-3 Polyunsaturated Fatty Acids Down-Modulate CXCR4 Expression and Function in MDA-MB-231 Breast Cancer Cells. Mol Cancer Res 2009; 7:1013-1020.
17. Mackinnon W B, Huschtscha L, Dent K, Hancock R, Paraskeva C, Mountford C E. Correlation of cellular differentiation in human colorectal carcinoma and adenoma cell lines with metabolite profiles determined by 1H magnetic resonance spectroscopy. International Journal of Cancer 1994; 59:248-261.
18. Mackinnon W B, May G L, Mountford C E. Esterified cholesterol and triglyceride are present in plasma membranes of Chinese hamster ovary cells. European Journal of Biochemistry 1992; 205:827-839.
19. Wright L C, Dyne M, Holmes K T, Mountford C E. Phospholipid and ether linked phospholipid content alter with cellular resistance to vinblastine. Biochemical & Biophysical Research Communicationsmackinn 1985; 133:539-545.
20. Bathen T F, Jensen L R, Sitter B, et al. MR-determined metabolic phenotype of breast cancer in prediction of lymphatic spread, grade, and hormone status. Breast Cancer Res Treat. 104(2):181-9 2007; 104.
21. Mountford C, Ramadan S. Two Dimensional Magnetic Resonance Spectroscopy on Biopsy and In Vivo. In: Webb G, ed. Progress in NMR, 2009.
22. Stanwell P, Mountford C, ISBN: 193188417X. In vivo proton magnetic resonance spectroscopy of the breast: Lippincott Williams & Wilkins, 2009.
23. Stanwell P, Gluch L, Clark D, et al. Specificity of choline metabolites for in vivo diagnosis of breast cancer using 1H MRS at 1.5T. European Radiology 2004.
24. Ramadan S, Ratai E M, Wald L L, Mountford C E. In vivo 1D and 2D correlation MR spectroscopy of the soleus muscle at 7T. J Magn Reson 2010; 204:91-98.
25. Velan S S, Lemieux S K, Raylman R R, et al. Detection of cerebral metabolites by single-voxelbased PRESS and COSY techniques at 3T. Journal of Magnetic Resonance Imaging 2007; 26:405-409.
26. Stanwell P, Gluch L, Clark D, et al. Specificity of choline metabolites for in vivo diagnosis of breast cancer using 1H MRS at 1.5T. European Radiology 2005; 15:1037-1043.
27. Stanwell P, Mountford C. In Vivo Proton Magnetic Resonance Spectroscopy of the Breast. RadioGraphics 2007; 27:S253-S266.
28. Ramadan S, Malycha P, Baltzer P, et al. In Vivo L-COSY Distinguishes Lobular from Invasive Ductal Carcinoma European Journal of Radiology 2012; 81:S129-S131.
29. Lipnick S, Liu X, Sayre J, W. Bassett L, DeBruhl N, Thomas M A. Combined DCE-MRI and single-voxel 2D MRS for differentiation between benign and malignant breast lesions. NMR in Biomedicine 2010; 23:922-930.
30. Somorjai R L. Creating robust, reliable, clinically relevant classifiers from spectroscopic data. Biophys Rev 2009; 1:201-211.
31. Schnall M D, Blume J, Bluemke D A, et al. Diagnostic architectural and dynamic features at breast MR imaging: Multicenter study. Radiology 2006; 238:42-53.
32. Ogg R, Kinglsey P, Taylor J. WET, a T1- and B1-insensitive water-suppression method for in vivo localized 1H NMR spectroscopy. Journal of Magnetic Resonance B 1994; 104:1-10.
33. Govindaraju V, Young K, Maudsley A A. Proton NMR chemical shifts and coupling constants for brain metabolites. NMR in Biomedicine 2000; 13:129-153.
34. Lean C L, Mackinnon W B, Delikatny E J, Whitehead R H, Mountford C E. Cell-surface fucosylation and magnetic resonance spectroscopy characterization of human malignant colorectal cells. Biochemistry 1992; 31:11095-11105.
35. Ramadan S, Mountford C. Two Dimensional Magnetic Resonance Spectroscopy on Biopsy and In Vivo. In: Webb G, ed. Annual Reviews in NMR: Academic Press, 2009.

What is claimed is:

1. A method for determining if a subject is a carrier of a mutation in the BRCA1 and/or BRCA2 genes that leads to a predisposition to breast cancer, the method comprising:
   obtaining spectral data from breast tissue obtained from the subject using an MRS acquisition unit which obtains spectral data with a magnetic resonance spectroscopy device; and
   analyzing said spectral data using an analysis unit, with spectral processing software run on a workstation or desktop PC by comparing the spectral data with reference data for known healthy breast tissue, and determining that the subject is a carrier of a mutation in the BRCA1 and/or BRCA2 genes that leads to a predisposition to breast cancer if the spectral data obtained identifies at least one of (1) a change in the degree and extent of MR recordable lipid saturation or increase in triglyceride levels, (2) an increase in MR visible cholesterol, and (3) a change in type and level of metabolic substrates in the breast tissue from the subject compared to reference values of MR recordable lipid saturation or triglyceride levels, MR visible cholesterol and/or metabolic substrates for healthy breast tissue.

2. The method of claim 1, wherein the spectral data is obtained using either 1D MRS or 2D COSY.

3. The method of claim 1, wherein the spectral data produced enables detection of increased unsaturated lipid and increased MR visible cholesterol, which is conducive to tumor growth and which constitutes a predisposition to breast cancer.

4. The method of claim 1, wherein the step of obtaining spectral data includes producing a spectral image on a display.

5. The method of claim 1, wherein the step of obtaining spectral data is performed in vivo.

6. The method of claim 1, wherein the step of obtaining spectral data is performed ex vivo.

7. A system for determining if a subject is a carrier of a mutation in the BRCA1 and/or BRCA2 genes that leads to a predisposition to breast cancer, the system comprising:
   an MRS acquisition unit for obtaining spectral data by magnetic resonance from breast tissue obtained from the subject; and
   an analysis unit, with spectral processing software run on a workstation or desktop PC, for analyzing said spectral data by comparing the spectral data with reference data for known healthy breast tissue, and determining that the subject is a carrier of a mutation in the BRCA1 and/or BRCA2 genes that leads to a predisposition to breast cancer if the spectral data identifies at least one of (1) a change in the degree and extent of MR recordable lipid saturation or an increase in triglyceride levels, (2) an increase in MR visible cholesterol, and (3) a change in type and level of metabolic substrates in the breast tissue from the subject compared to reference values of MR recordable lipid saturation or triglyceride levels, MR visible cholesterol and/or metabolic substrates for healthy breast tissue.

8. The system of claim 7, wherein the MRS acquisition unit obtains spectral data using either 1D MRS or 2D COSY.

9. The system of claim 7, wherein the MRS acquisition unit obtains spectral data which enables the analysis unit to detect increased unsaturated lipid and increased MR visible cholesterol, which is conducive to tumor growth and which constitutes a predisposition to breast cancer or the final stages prior to a malignant transformation occurring.

10. The system of claim 7, further including a display for displaying the spectral data.

11. The system of claim 7, wherein the MRS acquisition unit obtains spectral data in vivo.

12. The system of claim 7, wherein the MRS acquisition unit obtains spectral data ex vivo.

\* \* \* \* \*